United States Patent [19]

Narayanan et al.

[11] 3,956,285
[45] May 11, 1976

[54] CERTAIN OXY-AMINO-ALKOXY-5,8-DIHYDRONAPHTHALENES

[75] Inventors: Venkatachala Lakshmi Narayanan, Hightstown; Linda Louise Setescak, Cranbury; Frank Lee Weisenborn, Somerset, all of N.J.

[73] Assignee: E. R. Squibb & Sons, Inc., Princeton, N.J.

[22] Filed: Mar. 6, 1972

[21] Appl. No.: 232,286

Related U.S. Application Data

[60] Continuation-in-part of Ser. No. 5,993, Jan. 26, 1970, Pat. No. 3,668,206, which is a division of Ser. No. 768,176, Oct. 16, 1968, Pat. No. 3,534,085.

[52] U.S. Cl. .................. 260/243 B; 260/247.2 B; 260/247.7 Z; 260/326.33; 260/326.5 C
[51] Int. Cl.² ..................................... C07D 295/08
[58] Field of Search ............ 260/326.5 M, 247.7 C, 260/243 B, 326.33, 247.2 B, 326.5 C

[56] References Cited
UNITED STATES PATENTS

| | | | |
|---|---|---|---|
| 3,534,085 | 10/1970 | Narayanan et al. | 260/326.5 M |
| 3,668,206 | 6/1972 | Narayanan et al. | 260/268 BC |

Primary Examiner—Richard J. Gallagher
Attorney, Agent, or Firm—Lawrence S. Levinson; Merle J. Smith

[57] ABSTRACT

This invention relates to new 5,8-dihydronaphthyloxy-amino propanols and related compounds of the formula

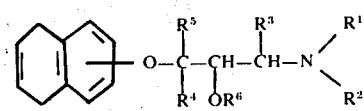

wherein the radical

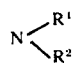

represents pyrrolidino and other heterocyclics, and to salts of each compounds, products which are useful in coronary diseases, water softening and corrosion inhibition.

6 Claims, No Drawings

CERTAIN OXY-AMINO-ALKOXY-5,8-DIHYDRONAPHTHALENES

This application is a continuation-in-part of application Ser. No. 5993, filed Jan. 26, 1970, now U.S. Pat. No. 3,668,206, issued June 6, 1972, which is in turn a division of application Ser. No. 768,176, filed Oct. 16, 1968, now U.S. Pat. No. 3,534,085, issued Oct. 13, 1970.

SUMMARY OF THE INVENTION

This invention relates to new chemical compounds of the formula (I) 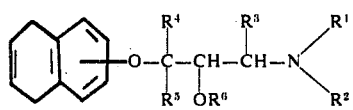

wherein the radical

is pyrrolidino, morpholino or thiamorpholino or members of that group with certain ring substituents, $R^3$, $R^4$ and $R^5$ each is hydrogen or lower alkyl, $R^6$ is hydrogen or the acyl radical of a hydrocarbon carboxylic acid of less than 14 carbon atoms, and salts of those compounds.

DETAILED DESCRIPTION OF THE INVENTION

In the substituents in formula I, the lower alkyl groups represented by the various symbols include straight and branched chain saturated hydrocarbon groups such as methyl, ethyl, propyl, isopropyl, butyl, isobutyl, t-butyl, amyl and the like. The phenyl-lower alkyl groups, also referred to below, include similar alkyl groups, e.g., benzyl, phenethyl and the like.

The acyl radicals represented by $R^6$ include lower fatty acid radicals such as acetyl, propionyl, butyryl, isobutyryl and the like, as well as long chain fatty acid radicals such as hexanoyl, heptanoyl, decanoyl, dodecanoyl and the like, aryl and aralkanoic acid radicals such as benzoyl, phenacetyl and the like.

The basic nitrogen containing radical (II) 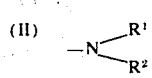

represents the heterocyclics pyrrolidino, morpholino and thiamorpholino. The heterocyclic group may also be substituted by one or two of the groups lower alkyl or lower alkoxy.

Thus heterocyclic groups represented by the radical II include for example, pyrrolidino, (lower alkyl) pyrrolidino, e.g., 2-methylpyrrolidino, di(lower alkyl) pyrrolidino, e.g., 2,3-dimethylpyrrolidino, (lower alkoxy) pyrrolidino, e.g., 2-ethoxypyrrolidino, morpholino, (lower alkyl) morpholino, e.g., N-methylmorpholino or 2-methylmorpholino, di(lower alkyl) morpholino, e.g., 2,3-dimethylmorpholino, (lower alkoxy) morpholino, e.g., 2-ethoxymorpholino, thiamorpholino, (lower alkyl) thiamorpholino, e.g., 2-methylthiamorpholino or 3-methylthiamorpholino, di(lower alkyl)-thiamorpholino, e.g., 2,3-diethylthiamorpholino, 2,3-dimethylthiamorpholino or (lower alkoxy) thiamorpholino, e.g., 2-methoxythiamorpholino.

In the foregoing radicals, the lower alkyl and lower alkoxy groups include straight and branched chain groups such as methyl, ethyl, propyl, isopropyl, butyl, isobutyl, t-butyl, methoxy, ethoxy, isopropoxy, butoxy, respectively.

The compounds of formula I form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic or organic acid. Illustrative are the hydrohalides, especially the hydrochloride and hydrobromide which are preferred, sulfate, nitrate, phosphate, borate, acetate, oxalate, tartrate, maleate, citrate, succinate, benzoate, ascorbate, salicylate, methanesulfonate, benzenesulfonate, toluenesulfonate and the like.

Preferred are those compounds wherein $R^3$, $R^4$, $R^5$ and $R^6$ are all hydrogen, the heterocyclic is unsubstituted pyrrolidino, morpholino or thiamorpholino, especially morpholino, particularly when the side chain is attached to the 1-position of the fused ring.

The new compounds of this invention are useful as water softeners and for inhibiting the corrosivity of the engine lubricants.

They are also useful as antifibrillatory agents, for example, in arresting cardiac arrhythmia in animals, e.g., by inhibition of beta adrenergic receptors in the myocardium. For this purpose a compound of formula I or a physiologically acceptable acid addition salt may be incorporated in a conventional dosage form such as tablet, capsule, elixir, injectable or the like along with the necessary carrier material, excipient, lubricant, buffer or the like. Single or divided doses of about 5 to 25 mg/kg/day, preferably about 4 to 10 mg/kg, two to four times daily may be administered in dosage forms as described above.

The products of formula I may be produced by either of two methods described below. The symbols have the same meanings defined previously.

According to the preferred method, a naphthol of the formula (III)

is reduced with a metal like sodium or lithium in liquid ammonia containing an alcohol such as ethanol, isopropanol, t-butanol or the like [e.g., by the procedure described in Organic Syntheses, Coll. Vol. 4, page 887 (1963)] to obtain the 5,8-dihydronaphthol of the formula (IV)

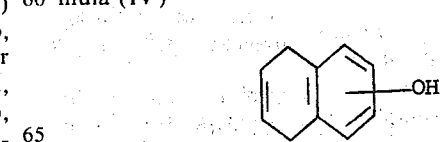

The compound of formula IV is made to react with an epoxide of the formula (V) 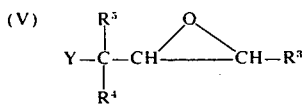

(Y is chlorine or bromine), to obtain a product of the formula (VI) 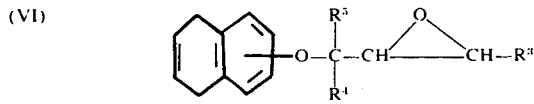

By refluxing the compound of formula VI with an amine of the formula

in an inert organic solvent such as n-propanol, benzene or toluene, e.g., for about 16 to 24 hours, yields a product of formula I wherein $R^6$ is hydrogen. An alternate procedure involves heating the reactants in a Paar pressure reactor at a temperature of about 70°– 110° for 6 – 12 hours. The ester, i.e., wherein $R^6$ is acyl is obtained by esterifying the product of the foregoing procedure with an appropriate hydrocarbon carboxylic acid, e.g., by refluxing the alcohol (formula I wherein $R^6$ =H) with the appropriate acid in a solvent like methylene or ethylene chloride using a trace of sulfuric, aryl sulfonic acid or borontrifluoride as catalyst. In an alternate procedure, the alcohol is heated with the appropriate acid chloride or acid anhydride (obtained from the appropriate hydrocarbon carboxylic acid) in the presence of anhydrous pyridine or sodium acetate. Examples of such acids include acetic acid, propionic acid, butyric acid, isobutyric acid, hexanoic acid, decanoic acid, benzoic acid, phenylacetic acid, etc. The acid addition salts may be formed as previously described.

As an alternate method, an amine of formula VII is reacted with a compound of the formula (VIII) 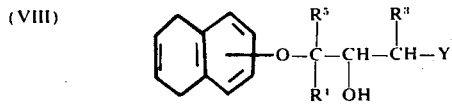

(Y is halogen, preferably bromine), e.g., by refluxing two equivalents of the amine of formula VII with one equivalent of VIII in an organic solvent such as chloroform, benzene, toluene or dimethoxyethane for about 6 to 10 hours.

The compounds of formula VIII are prepared by reacting compounds of formula VI with a hydrohalic acid, for example, hydrobromic acid.

The following examples are illustrative of the invention. All temperatures are on the centigrade scale.

EXAMPLE 1

1-(5,8-Dihydro-1-naphthyloxy)-3-pyrrolidino)-2-propanol a) 5,8-dihydro-1-naphthol A 3 l. three necked flask, equipped with a Dry Ice condenser, a sealed Hershberg-type stirrer, and an inlet tube, is set up in a hood and charged with 108 g. (0.75 mole) of α-naphthol. The stirrer is started, and to the rapidly stirred flask contents is added 1 l. of liquid ammonia as rapidly as possible (about 5 minutes). When the naphthol has gone into solution (about 10 minutes), 20.8 g. (3.0 g. atoms) of lithium metal is added in small pieces and at such a rate as to prevent the ammonia from refluxing too violently. After the addition of the lithium has been completed (about 45 minutes), the solution is stirred for an additional 20 minutes and is then treated with 170 ml. (3.0 moles) of absolute ethanol which is added dropwise over a period of 30–45 minutes. The condenser is removed, stirring is continued, and the ammonia is evaporated in a stream of air introduced through the inlet tube. The residue is dissolved in 1 l. of water, and, after the solution has been extracted with two 100 ml. portions of ether, it is carefully acidified with concentrated hydrochloric acid. The product formed is taken into ether with three 250 ml. extractions, and then the ether extract is washed with water and dried over anhydrous sodium sulfate. The ether is removed by evaporation to yield 106 – 108 g. (97–99%) of crude 5,8-dihydro-1-naphthol, m.p. 69°–72°. This material is dissolved in benzene, treated with charcoal, the solvent is evaporated, and the residue crystallized from hexane to give pure 5,8-dihydro-1-naphthol, m.p. 70.5° – 72°.

b. 1-(2,3-epoxypropoxy)-5,8-dihydronaphthalene

To a cooled solution of 15 g. (0.1 m.) of 5,8-dihydro-1-naphthol and 13.2 g. (0.14 m.) of epichlorohydrin in 38 ml. of p-dioxane, a cold solution of 4.9 g. of sodium hydroxide in 10 ml. of water is added dropwise. The mixture is refluxed three hours, cooled, and extracted with benzene. The benzene extract is washed with water, dried (MgSO$_4$) and evaporated in vacuo to give 1-(2,3-epoxypropoxy)-5,8-dihydronaphthalene. Distillation of the crude oil at 1.2 mm., b.p. 139°–140°, gives a colorless liquid; $\lambda_{liq.}^{max.}$ film 1250, 910, 840 cm$^{-1}$ (characteristic epoxy bands), CDCl$_3$ 4.13 (-C/H=C/H-), 2.5 – 3.5 (aromatic protons).

c. 1-(5,8-dihydro-1-naphthyloxy)-3-(pyrrolidino)-2-propanol

A mixture of 4.4 g. (0.02 m.) of product of part b and 14.2 g. (0.2 m.) of pyrrolidine is placed in a small Parr pressure reactor and heated in an oil bath (bath temp. 80°–86°- pressure gauge registered 50 psi) for 10 hours. After standing overnight excess pyrrolidine is evaporated in vacuo to give 1-(5,8-dihydro-1-naphthyloxy)-3-(pyrrolidino)-2-propanol.

EXAMPLE 2

1-(5,8-Dihydro-1-naphthyloxy)-3-(pyrrolidino)-2-propyl acetate

A mixture of 3 g. of 1-(5,8-dihydro-1-naphthyloxy)-3-(pyrrolidino)-2-propanol, 1.5 g. of fused acetate and 15 ml. of acetic anhydride is heated on a steam bath with occasional shaking for one hour. At the end of this time, the warm solution is poured with vigorous stirring into 100 ml. of ice water. The mixture is stirred for 10-15 minutes and the crystals of 1-(5,8-dihydro-1- naphthyloxy)-3-(pyrrolidino)-2-propyl acetate are collected, washed thoroughly with water, and purified by crystallization from alcohol.

EXAMPLE 3

By substituting β-naphthol for the α-naphthol in part a in Example 1, 1-(5,8-dihydro-2-naphthyloxy)-3-(pyrrolidino)-2-propanol is obtained.

In addition by following the procedure of Example 1, utilizing the α- or β-naphthol indicated below in part a and substituting the heterocyclic indicated below for the pyrrolidine in part c, there is obtained the corresponding 1-(5,8-dihydro-1(or 2)-naphthyloxy-3-substituted pyrrolidino)-2-propanol having the

group corresponding to the amine listed:

| Example | naphthol | pyrrolidine |
|---|---|---|
| 4 | α | 2-methylpyrrolidine |
| 5 | β | 2,3-dimethylpyrrolidine |
| 6 | β | 2,3-diethylpyrrolidine |
| 7 | β | 2-ethoxypyrrolidine |

EXAMPLE 8 – 12

Following the procedure of Example 1, but substituting for 1-(2,3-epoxypropoxy)-5,8-dihydronaphthalene in part c the substituted compound of the following formula, there is obtained 1-(5,8-dihydro-1-naphthyloxy)-3-pyrrolidino-2-propanol having the same substituents $R^3$, $R^4$ and $R^5$.

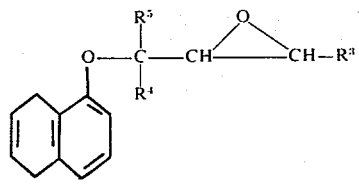

| Example | $R^3$ | $R^4$ | $R^5$ |
|---|---|---|---|
| 8 | H | $CH_3$ | H |
| 9 | $C_2H_5$ | H | H |
| 10 | $CH_3$ | H | $C_2H_5$ |
| 11 | $CH_3$ | $CH_3$ | H |
| 12 | $CH_3$ | $CH_3$ | $CH_3$ |

EXAMPLE 13

2-(5,8-dihydro-1-naphthyloxy)-2-methyl-4-(1-pyrrolidino)-3-pentanol

By following the procedure of Example 1, but substituting 2-(5,8-dihydro-1-naphthyloxy)-2-methyl-3,4-epoxy)pentane for the epichlorhydrin in part b, 2-(5,8-dihydro-1-naphthyloxy)-2-methyl-4-(pyrrolidino)-3-pentanol is obtained.

EXAMPLES 14 – 18

Following the procedure of Example 1, but substituting β-naphthol for α-naphthol in part a and substituting for the 1-(2,3-epoxypropoxy)-5,8-dihydronaphthalene in part c, the substituted compound of the following formula, there is obtained the substituted 1-(5,8-dihydro-2-naphthyloxy)-3-pyrrolidino-2-propanol having the same substituents $R^3$, $R^4$ and $R^5$.

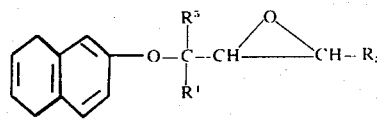

| Example | $R^3$ | $R^4$ | $R^5$ |
|---|---|---|---|
| 14 | H | $CH_3$ | H |
| 15 | $CH_3$ | H | H |
| 16 | $CH_3$ | $CH_3$ | H |
| 17 | $CH_3$ | $CH_3$ | $CH_3$ |
| 18 | $C_2H_5$ | H | $C_2H_5$ |

EXAMPLE 19

1-(5,8-dihydro-1-naphthyloxy)-3-(morpholino)-2-propanol

Following the procedure of Example 1, but substituting an equivalent amount of morpholine for pyrrolidine in part c, there is obtained 1-(5,8-dihydro-1-naphthyloxy)-3-(morpholino)-2-propanol.

EXAMPLES 20 – 23

Following the procedure of Examples 1 and 19, but substituting β-naphthol for the β-naphthol in part a, 1-(5,8-dihydro-2-naphthyloxy)-3-(morpholino)-2-propanol is obtained.

In addition by following the procedure of Examples 1 and 19, utilizing the α- or β-naphthol indicated below in part a and replacing the substituted morpholine indicated below for the morpholine in part c, there is obtained the corresponding 1-(5,8-dihydro-(1- or 2)-naphthyloxy)-3-(substituted morpholino)-2-propanol.

| Example | naphthol | morpholine |
|---|---|---|
| 21 | β | 2-methylmorpholine |
| 22 | α | 2,3-dimethylmorpholine |
| 23 | β | 2-ethoxymorpholine |

EXAMPLES 24 – 28

Following the procedure of Examples 1 and 19, but substituting for 1-(2,3-epoxypropoxy)-5,8-dihydronaphthalene in part c, the substituted compound of the following formula, there is obtained 1-(5,8-dihydro-1-naphthyloxy)-3-morpholino-2-propanol having the same substituents $R^3$, $R^4$ and $R^5$.

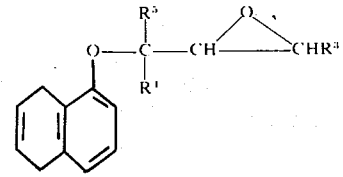

| Example | $R^3$ | $R^4$ | $R^5$ |
|---|---|---|---|
| 24 | H | $CH_3$ | H |
| 25 | $CH_3$ | H | H |
| 26 | $CH_3$ | $CH_3$ | H |
| 27 | $CH_3$ | $CH_3$ | $CH_3$ |
| 28 | H | $C_2H_5$ | H |

EXAMPLES 29 – 33

Following the procedure of Examples 1 and 19, but substituting β-naphthol for α-naphthol in part a and substituting for the 1-(2,3-epoxypropoxy)-5,8-dihydronaphthalene in part c, the substituted compound of the following formula, there is obtained the substituted 1-(5,8-dihydro-2-naphthyloxy)-3-morpholino-2-propanol having the same substituents $R^3$, $R^4$ and $R^5$.

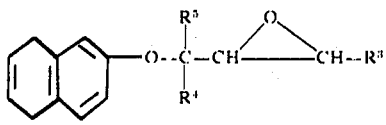

| Example | $R^3$ | $R^4$ | $R^5$ |
|---|---|---|---|
| 29 | H | $CH_3$ | H |
| 30 | $C_2H_5$ | H | H |
| 31 | $CH_3$ | $CH_3$ | H |
| 32 | $CH_3$ | $CH_3$ | $CH_3$ |
| 33 | H | $C_2H_5$ | H |

EXAMPLE 34

1-(5,8-dihydro-1-naphthyloxy)-3-(thiamorpholino)-2-propanol

Following the procedure of Example 1, but substituting an equivalent amount of thiamorpholine for pyrrolidine in part c, there is obtained 1-(5,8-dihydro-1-naphthyloxy)-3-(thiamorpholino)-2-propanol.

EXAMPLES 35 – 39

Following the procedure of Example 34, but substituting β-naphthol for the α-naphthol in part a, 1-(5,8-dihydro-2-naphthyloxy)-3-(thiamorpholino)-2-propanol is obtained.

In addition by following the procedure of Examples 1 and 34, utilizing the α- or β-naphthol indicated below in part a and substituting the substituted thiamorpholine indicated below for the thiamorpholine in part c, there is obtained the corrresponding 1-(5,8-dihydro-(1- or 2-)-naphthyloxy)-3-(substituted thiamorpholino)-2-propanol.

| Example | naphthol | thiamorpholine |
|---|---|---|
| 36 | α | 2-methylthiamorpholine |
| 37 | β | 2,3-diethylthiamorpholine |
| 38 | α | 2,3-dimethylthiamorpholine |
| 39 | α | 2-methoxythiamorpholine |

EXAMPLES 40 – 44

Following the procedure of Examples 1 and 34, but substituting for 1-(2,3-epoxypropoxy)-5,8-dihydronaphthalene in part c, the substituted compound of the following formula, there is obtained 1-(5,8-dihydro-1-naphthyloxy)-3-thiamorpholino-2-propanol having the same substituents $R^3$, $R^4$ and $R^5$.

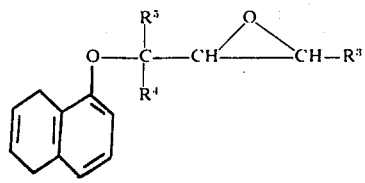

| Example | $R^3$ | $R^4$ | $R^5$ |
|---|---|---|---|
| 40 | H | $CH_3$ | H |
| 41 | $C_2H_5$ | H | H |
| 42 | $CH_3$ | $CH_3$ | H |
| 43 | $CH_3$ | $CH_3$ | $CH_3$ |
| 44 | H | $C_2H_5$ | H |

EXAMPLES 45 – 48

Following the procedure of Examples 1 and 34, but substituting β-naphthol for the α-naphthol in part a and substituting for the 1-(2,3-epoxypropoxy)-5,8-dihydronaphthalene in part c the substituted compound of the following formula, there is obtained the substituted 1-(5,8-dihydro-2-naphthyloxy)-3-thiamorpholino-2-propanol having the same substituents $R^3$, $R^4$ and $R^5$.

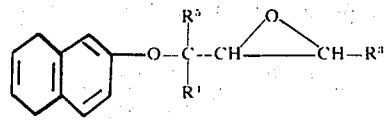

| Example | $R^3$ | $R^4$ | $R^5$ |
|---|---|---|---|
| 45 | H | $CH_3$ | H |
| 46 | $C_2H_5$ | H | H |
| 47 | $CH_3$ | $CH_3$ | H |
| 48 | $CH_3$ | $CH_3$ | $CH_3$ |

By esterifying the product of each of the foregoing examples with acetic acid, propionic acid, butyric acid, decanoic acid, dodecanoic acid, phenylacetic acid, phenylpropionic acid and phenylbutyric acid, respectively, as described in Example 2, the acetate, propionate, butyrate, decanoate, dodecanoate, phenylacetate, phenylpropionate and phenylbutyrate of each is obtained.

What is claimed is:

1. A compound of the formula

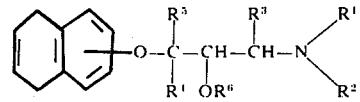

wherein the radical

is pyrrolidino, morpholino, thiamorpholino, or said radicals substituted by one or two $C_1$-$C_4$ alkyl groups or one $C_1$-$C_4$ alkoxy group, $R^3$, $R^4$ and $R^5$ each is hydrogen or $C_1$-$C_4$ alkyl and $R^6$ is hydrogen, $C_2$-$C_{12}$ alkanoyl, phenacetyl or benzoyl, and physiologically acceptable acid addition salts of said compounds.

2. A compound as in claim 1 wherein $R^3$, $R^4$, $R^5$ and $R^6$ each is hydrogen.

3. A compound as in claim 2 wherein the ring attachment is in the 1-position.

4. A compound as in claim 3 wherein the radical

is morpholino.

5. A compound as in claim 2 wherein the radical
is thiamorpholino and the ring attachment is in the 2-position.
6. A compound as in claim 3 wherein the radical
is 2-methylpyrrolidino.
* * * * *